(12) United States Patent
Kuroda et al.

(10) Patent No.: US 9,849,427 B2
(45) Date of Patent: Dec. 26, 2017

(54) HOLLOW FIBER MEMBRANE FOR BLOOD PURIFICATION AND BLOOD PURIFICATION APPARATUS USING THE SAME

(75) Inventors: Mariko Kuroda, Miyazaki (JP); Masaya Fuke, Oita (JP); Masaki Katou, Miyazaki (JP)

(73) Assignee: ASAHI KASEI MEDICAL CO., LTD., Tokyo (JP)

(*) Notice: Subject to any disclaimer, the term of this patent is extended or adjusted under 35 U.S.C. 154(b) by 449 days.

(21) Appl. No.: 10/579,449

(22) PCT Filed: Nov. 17, 2004

(86) PCT No.: PCT/JP2004/017082
§ 371 (c)(1),
(2), (4) Date: Aug. 16, 2006

(87) PCT Pub. No.: WO2005/046763
PCT Pub. Date: May 26, 2005

(65) Prior Publication Data
US 2007/0080108 A1    Apr. 12, 2007

(30) Foreign Application Priority Data

Nov. 17, 2003 (JP) .............................. P2003-386582
Feb. 6, 2004 (JP) .............................. P2004-030160

(51) Int. Cl.
*B01D 67/00* (2006.01)
*A61M 1/18* (2006.01)
(Continued)

(52) U.S. Cl.
CPC .......... *B01D 69/02* (2013.01); *B01D 67/0011* (2013.01); *B01D 69/08* (2013.01);
(Continued)

(58) Field of Classification Search
USPC .......................... 210/500.23, 500.41, 500.42
See application file for complete search history.

(56) References Cited

U.S. PATENT DOCUMENTS 4,906,375 A * 3/1990 Heilmann ................. 210/500.23
5,338,814 A * 8/1994 Wu et al. ....................... 526/210
(Continued)

FOREIGN PATENT DOCUMENTS

CN     1150918      6/1997
CN     1101310 C    2/2003
(Continued)

OTHER PUBLICATIONS

Cameo Chemicals PVP-K90 reference—Cameo Chemicals is an online database of hazardous materials maintained by the US government. PVP-K90 reference is available at http://www.cameochemicals.noaa.gov/report/?chem_id=20942.*

(Continued)

*Primary Examiner* — Bobby Ramdhanie
*Assistant Examiner* — Denise R Anderson
(74) *Attorney, Agent, or Firm* — Greenblum & Bernstein, P.L.C.

(57) ABSTRACT

An object of the present invention is to provide a hollow fiber membrane with enhanced phosphorus-removing performance without impairing antithrombogenicity in order to inhibit in vivo accumulation of phosphate ions in living body that might cause bone metabolism disorders.

The present inventors have found that a hollow fiber membrane having a specific membrane structure and a specific membrane composition possesses a very useful range for inner surface charges of the membrane. More particularly, the inventors have discovered that the above object can be achieved in a limited range in which the zeta potential on the inner surface of a hollow fiber membrane measured under (Continued)

given certain conditions is greater than −3.0 mV but less than 0 mV. This finding has led to the completion of the present invention.

13 Claims, 1 Drawing Sheet

(51) Int. Cl.

| | | |
|---|---|---|
| *B01D 69/02* | (2006.01) | |
| *B01D 69/08* | (2006.01) | |
| *B01D 69/12* | (2006.01) | |
| *B01D 71/34* | (2006.01) | |
| *B01D 71/44* | (2006.01) | |
| *B01D 71/68* | (2006.01) | |
| *A61M 1/16* | (2006.01) | |

(52) U.S. Cl.
CPC ........... *B01D 69/084* (2013.01); *B01D 71/34* (2013.01); *B01D 71/68* (2013.01); *A61M 1/16* (2013.01); *B01D 2325/023* (2013.01); *B01D 2325/04* (2013.01); *B01D 2325/26* (2013.01)

(56) References Cited

U.S. PATENT DOCUMENTS

| | | | | |
|---|---|---|---|---|
| 5,407,581 | A | | 4/1995 | Onodera et al. |
| 5,474,680 | A | * | 12/1995 | Eguchi ................. 210/500.23 |
| 5,683,584 | A | * | 11/1997 | Wenthold et al. ....... 210/500.23 |
| 5,762,798 | A | * | 6/1998 | Wenthold et al. ....... 210/500.23 |
| 5,938,929 | A | * | 8/1999 | Shimagaki et al. .......... 210/645 |
| 6,103,117 | A | * | 8/2000 | Shimagaki et al. ...... 210/321.71 |
| RE36,914 | E | * | 10/2000 | Carlsen et al. .......... 210/321.79 |
| 6,355,730 | B1 | * | 3/2002 | Kozawa et al. ............. 525/189 |
| 6,432,309 | B1 | * | 8/2002 | Fuke et al. ............... 210/500.41 |
| 6,802,971 | B2 | * | 10/2004 | Gorsuch et al. ......... 210/500.23 |
| 2004/0167237 | A1 | * | 8/2004 | Kim et al. ...................... 521/50 |

FOREIGN PATENT DOCUMENTS

| | | | |
|---|---|---|---|
| EP | 0 750 938 | 1/1997 | |
| EP | 0 997 182 | 5/2000 | |
| EP | 1388364 | 2/2004 | |
| EP | 1 410 839 | 4/2004 | |
| JP | 4-007024 | 1/1992 | |
| JP | 4-300636 | 10/1992 | |
| JP | 6-7431 | 1/1994 | |
| JP | 9-70524 | 3/1997 | |
| JP | 10-243999 | 9/1998 | |
| JP | 11-332980 | 7/1999 | |
| JP | 2002-253938 | 10/2002 | |
| JP | 2003-033432 | 2/2003 | |
| WO | 98/25758 | 6/1998 | |
| WO | WO0178805 A1 * | 10/2001 | .............. A61M 1/16 |
| WO | 02/087735 | 11/2002 | |

OTHER PUBLICATIONS

Humidity Calculator, http://www.humidity-calculator.com/index.php, accessed on Oct. 17, 2009.*
English Language Abstract of JP 4-007024.
English Language Abstract of JP 10-243999.
English Language Abstract of JP 4-300636.
English Language Abstract of JP 2003-033432.
"The high performance membrane for hemodialysis stuff", Tokyo Igakusha Co., Ltd., pp. 130-131 (1990).
Chinese Office Action issued with respect to Chinese Patent App. No. 201010166796.X dated Dec. 24, 2010.
Taiwan Office action, dated Jun. 20, 2011.
German Communication of a notice of opposition dated May 16, 2013 along with an English Translation.

\* cited by examiner

HOLLOW FIBER MEMBRANE FOR BLOOD PURIFICATION AND BLOOD PURIFICATION APPARATUS USING THE SAME

TECHNICAL FIELD

The present invention relates to a hollow fiber membrane for blood purification and a blood purification apparatus including the same. More particularly, the invention relates to a hollow fiber membrane that can be used for medical treatment of renal failure and the like and exhibits excellent biocompatibility and solute removing performance, and to a blood purification apparatus using the hollow fiber membrane.

BACKGROUND ART

As a blood purification therapy using a hollow fiber membrane, medical treatment of chronic renal failure by hemodialysis, an apheresis treatment, and the like are widely performed. Especially, in the field of hemodialysis treatment, the number of hemodialysis patients has considerably increased with the progress in the method of treatment. For example, the number of dialysis patients in Japan has already exceeded 200,000 and the number of hemodialysis patients on a long-term basis is also increasing. In these circumstances, various dialysis complications, such as disorders caused by accumulation of uremic substances in specific sites or organs following a long dialysis period, metabolic disorders resulting from improper removal of specific uremic substances, and the like, are acknowledged as problems. A medical treatment for improving the quality of life (QOL) of the dialysis patients by positively removing uremic substances leading to a dialysis complication is being tested.

On the basis of these purpose, a number of studies on hollow fiber membranes for blood purification are ongoing with the objective of improving permeability of specific substances through the membrane by reviewing the structure, composition, and properties of hollow fiber membranes. Specific examples of such studies include a study for increasing pore size of the membrane for removing uremic proteins (also referred to as "low-molecular-weight proteins"), a study for improving fractionability of the membrane for permeating low-molecular-weight proteins with a molecular weight smaller than biologically useful albumin, while inhibiting permeation or loss of such useful substances, and a study for improving membrane surface properties of selectively permeating not only such low-molecular-weight proteins, but also charged low-molecular-weight nonprotein uremic substances.

Of the complications actualized by a long-term dialysis treatment, dialysis amyloidosis is a well known typical example of the complication which is caused by uremic low-molecular-weight proteins. In an effort to combat the dialysis amyloidosis, various studies have been undertaken to increase sharpness of fractionability of hollow fiber membranes by improving the membrane's capability of removing $\beta_2$-Microglobulin, which is a substance causing the dialysis amyloidosis, while inhibiting permeation of biologically useful albumin. In addition, with an objective of more efficiently ameliorating the dialysis amyloidosis, a study for removing $\alpha_1$-microglobulin, which is a uremic low-molecular-weight protein similar to $\beta_2$-microglobulin, is ongoing.

For example, Patent document 2 discloses a membrane with an improved permeation balance and a high water permeability, while inhibiting leakage of proteins, by localizing hydrophilic polymer in a dense layer near the inner surface of the membrane. However, this membrane is not satisfactory due to permissive requirement for albumin permeation as evidenced by the description in paragraph [0062] of the document 2 stating that "non-permeability of albumin is defined as having an albumin permeation rate of 5% or less". The description only mentions that the amount of leaked albumin is small in relation to water permeability, which is a technique simply achievable by a small pore diameter, and the document does not describe or suggest the capability of fractionating into different low-molecular-weight proteins. Thus, usefulness of the invention for improving the complication caused by long-term dialysis is not clear.

As prior art documents concretely disclosing capability of fractionating into low-molecular-weight proteins and albumin, Patent documents 3 and 4 can be given. Patent document 3 discloses a method for increasing selective separation performance of a membrane by enabling multi-layer filtration by increasing the thickness of a dense layer which functions as a selective separation layer by controlling membrane-forming conditions. According to this method, it is possible to inhibit albumin leakage in spite of the use of a membrane with a large pore diameter which permits sufficient removal of low-molecular-weight proteins. Patent document 4 discloses a blood purification membrane in which the permeation rate of polyvinylpyrrolidone with a molecular weight of 40,000 and the permeation rate of albumin are specified. The permeation rate of polyvinylpyrrolidone here is used as an index corresponding to the permeation rate of $\beta_2$-Microglobulin, which is a low-molecular-weight protein. The patent document 4 discloses a hollow fiber membrane that can remove the $\beta_2$-microglobulin while inhibiting permeation of albumin.

On the other hand, complications that are induced by not only accumulation of the low-molecular-weight proteins but also accumulation of uremic substances with a far smaller molecular weight than the low-molecular-weight proteins are known among the complications caused by long-term dialysis treatment. As a typical example, bone metabolism disorders induced by a high in vivo concentration of phosphate ion which is a charged inorganic substance can be given. In order to promote performance of membranes for removing phosphorus compounds which are causative substances, various studies on improvement mainly of surface properties of hollow fiber membranes are ongoing. Charges on the inner surface of a hollow fiber membrane coming in contact with blood are thought to be an important factor which determines the phosphorus-removing performance. A zeta potential is one of the indices expressing charges. It is known that the phosphorus-removing performance decreases when the zeta potential is negative and increases when the zeta potential is positive (Non-patent document 1). There is a report stating that, in general, when the zeta potential on the membrane surface is charged with positive charges of 0 mV or more, blood cells such as platelets, of which the cell membrane surface is negatively charged, are easily adsorbed on the membrane surface. Particularly, if platelets adhere and are activated, a blood coagulation system is activated and phenomena such as worsening of blood-remaining properties and the like easily occur, with a consequence of inferior antithrombogenicity.

Contrary, if a hollow fiber membrane having strong negative charges is used in a hemodialysis treatment, not only phosphorus-removing performance decreases due to electric repelling, but also the bradykinin value increases, giving rise to an anaphylactoid reaction. Since the bradykinin value further increases by the use of an ACE inhibitor, the use of a membrane strongly charged with negative charges requires stringent care. For this reason, in order to increase phosphorus-removing performance without impairing antithrombogenicity of a membrane, and yet inhibiting anaphylaxis, a membrane with a strictly controlled negative charge distribution and size of the charges was thought to be required.

Patent document 1, for example, describes a composite hollow fiber membrane which has negative charges on the inner surface and more positive charges toward the outer from the inner surface. However, the membrane does not exhibit sufficient phosphorus-removing performance because of a possible reason that the effect resulting from controlling appropriate negative charges on the inner surface has not been discovered. Specifically, although the document 1 describes the data that phosphorus clearance of a module with a membrane area of 1.0 $m^2$ is 132 ml/min, a phosphorus clearance rate for a membrane area of 1.5 $m^2$ equivalent calculated based on the overall mass transfer coefficient of phosphorus obtained from this value is found to be only as small as 156 ml/min. In addition, although the membrane disclosed in Patent document 4 is a polymer blend membrane containing a hydrophobic polymer and a hydrophilic polymer, it did not consider the charges on the inner surface. Non-patent document 1 describes a general concept of the zeta potential on the membrane surface and the phosphorus-removing performance as mentioned above, but the document does not present any direct suggestions on a system with more complicated membrane surface properties such a polymer blend membrane comprising a hydrophobic polymer and a hydrophilic polymer as disclosed in the present invention.

As described above, although various studies have been undertaken on the improvement of hollow fiber membranes for blood purification with an objective of ameliorating the complications caused by long-term dialysis, none of the efforts heretofore have been successful in obtaining a hollow fiber membrane that can satisfy the requirements for ameliorating each of the complications. In addition, the past studies focus their target exclusively on removal of the substance causing the individual complication in question and, therefore, have not found a hollow fiber membrane which is more effective for ameliorating complications by, for example, sufficiently removing charged inorganic substances while also sufficiently removing low-molecular-weight proteins.

[Patent document 1] Japanese Patent Application Laid-open No. 04-7024

[Patent document 2] Japanese Patent Application Laid-open No. 04-300636

[Patent document 3] Japanese Patent Application Laid-open No. 10-243999

[Patent document 4] Japanese Patent Application Laid-open No. 2003-33432

[Non-patent document 1] "The high performance membrane for hemodialysis stuff", Tokyo Igakusha Co., Ltd., pages 130-131 (1990)

DISCLOSURE OF THE INVENTION

Problems to be Solver by the Invention

In view of the present situation in the improvement of hollow fiber membranes used for various complications caused by long-term dialysis as mentioned above, and particularly an increase of hollow fiber membrane pore size in recent years, the present inventors have realized the necessity for removing low-molecular-weight inorganic substances to a greater extent, and insufficiency of the present level of technology for removing low-molecular-weight inorganic substances, and the inventors have realized that it is top priority to improve those points firstly. Specifically, a main object of the present invention is to provide a hollow fiber membrane with enhanced phosphorus-removing performance without impairing antithrombogenicity in order to inhibit in vivo accumulation of phosphate ions that cause bone metabolism disorders, and a blood purification apparatus using the hollow fiber membrane.

Means for Solving the Problems

The present inventors have conducted extensive studies to obtain a hollow fiber membrane for blood purification which does not impair antithrombogenicity, has only a low risk of side effects due to excessive negative charges, and exhibits excellent phosphorus-removing performance. As a result, the inventors have found that a hollow fiber membrane having a specific membrane structure and a specific membrane composition possesses a very useful range for inner surface charges of the membrane. More particularly, the inventors have discovered that the above object can be achieved in a limited range in which the zeta potential on the inner surface of a hollow fiber membrane measured under given certain conditions is greater than −3.0 mV but less than 0 mV. This finding has led to the completion of the present invention. Therefore, the present invention relates to:

(1) a hollow fiber membrane for blood purification comprising a hydrophobic polymer and a hydrophilic polymer, exhibiting a zeta potential on the inner surface thereof greater than −3.0 mV but less than 0 mV at pH 7.5, when measured using a sample with an embedded resin on the outer side for allowing the electrolyte solution to flow through only the inside of the hollow fiber, and using a 0.001 mol/l potassium chloride aqueous solution as an electrolyte solution;

(2) the hollow fiber membrane for blood purification according to (1), having:

(a) a polyvinylpyrrolidone sieving coefficient of 45% or more in a filtration test using a polyvinylpyrrolidone aqueous solution with a weight average molecular weight of 40,000, (b) an albumin sieving coefficient of 0.6% or less in a filtration test using bovine serum, (c) a protein adsorption amount of 65 mg/$m^2$ or less, (d) breaking strength of 60 kg/$cm^2$ or more, and (e) breaking elongation of 60% or more;

(3) the hollow fiber membrane for blood purification according to (1) or (2), wherein the hydrophobic polymer is a polysulfone-based resin;

(4) the hollow fiber membrane for blood purification according to any of (1) to (3), wherein the hydrophilic polymer is polyvinylpyrrolidone;

(5) the hollow fiber membrane for blood purification according to (4), further having: (f) the polyvinylpyrrolidone concentration in the hollow fiber membrane of 3.0 to 5.0 wt %;

(6) the hollow fiber membrane for blood purification according to (1) to (4), for having the overall mass transfer coefficient of phosphorus of 0.040 cm/min or greater;

(7) the hollow fiber membrane for blood purification according to any of (1) to (6), further having: (g) the thickness of the dense layer of 1 to 5 μm;

(8) a blood purification apparatus comprising the hollow fiber membrane according any of (1) to (7) installed in a cylindrical container having two nozzles for flowing a dialysate, the container having both ends fabricated with a potting material for separating the hollow inside of the membrane from the outside by a membrane wall and the container further having a header cap for flowing blood fitted on both ends; and (9) the blood purification apparatus according to (8), wherein the phosphorus clearance per membrane area of 1.5 cm$^2$ is 180 ml/min or more.

Effects of the Invention

According to the present invention, phosphorus-removing performance of a hollow fiber membrane for blood purification having a specific membrane structure and a specific membrane composition can be enhanced without impairing antithrombogenicity by limiting the inner surface zeta potential in a range greater than −3.0 mV but less than 0 mV.

In addition, the present inventors have discovered a hollow fiber membrane exhibiting not only excellent phosphorus-removing performance, but also superior capability of fractionating into low-molecular-weight proteins and albumin.

Therefore, the hollow fiber membrane and the blood purification apparatus using said hollow fiber membrane of the present invention are useful not only for bone metabolism disorder, but also for improvement of dialysis amyloidosis and the like, and are suitable for effectively improving complications caused by long-term dialysis.

EXPLANATION OF REFERENCES

1 Wavelength
2 Amplitude

BEST MODE FOR CARRYING OUT THE INVENTION

The present invention is described below in detail.

The hollow fiber membrane of the present invention has an integrally continuous structure from the inner surface to the outer surface and exhibits a zeta potential of greater than −3.0 mV but less than 0 mV at pH 7.5 which is equivalent to the pH of blood, when measuring the zeta potential using a 0.001 mol/l potassium chloride aqueous solution as an electrolyte solution. Therefore, the hollow fiber membrane exhibits promoted phosphorus removing performance while maintaining the antithrombogenicity. The structure of the hollow fiber membrane of the present invention is integrally continuous structure from the inner surface to the outer surface. "The integrally continuous structure from the inner surface to the outer surface" as referred to in the present invention means that hollow fiber membrane is produced from the same material continuously from the inner surface to the outer surface, differing from the composite hollow fiber membrane disclosed in the above-described Patent document 1, in which the outer surface has a chemical composition differing from the inner surface. In addition, the above definition of the present invention means that the chemical substance forming the entire membrane from the inner surface to the outer surface has the same primary structure, differing from the hollow fiber membrane disclosed in Patent document 1 in which the inner surface or the outer surface is chemically modified after preparation of the membrane.

In the hollow fiber membrane having the defined structure and composition, if the zeta potential is 0 mV or more, the membrane surface is positively charged and exhibits a rapid increase in the amount of negatively charged platelets and the like attached thereto, leading to a decrease in antithrombogenicity. This is a situation to be avoided. According to the finding by the present inventors, contrary, if the zeta potential is −3 mV or less, the phosphorus-removing performance rapidly decreases. In particular, when the phosphorus clearance is measured on a module in which the membrane is installed so that the membrane surface area is constant, the measured value changes five points or more at −3.0 mV as boundary. This change is not linearly proportional to the change of the zeta potential as described in Non-patent document 1. Although the detailed reason is not clear, it is thought that when the surface of a hydrophobic polymer which is generally negatively charged is masked with a hydrophilic polymer during a process of forming a membrane, some region on the surface may encounter a significant change of charges depending on the distribution and manner of installation of the hydrophilic polymer. Therefore, the phenomenon is thought to be not so simple as in such a membrane with a single composition as described in Non-patent document 1.

In the present invention, the state described by the term "while maintaining antithrombogenicity" preferably includes, but is not limited to, a state in which the number of attached platelets in the later-described platelet adhesion evaluation is $3.0 \times 10^4$/cm$^2$ or less, and more preferably $1.0 \times 10^4$/cm$^2$.

The zeta potential of the hollow fiber membrane of the present invention can be measured by the following method.

1) A sample is prepared from a bundle of hollow fiber membranes removed from a disassembled blood purification apparatus by cutting 1400±50 of the hollow fiber membranes into pieces having a length of 50±5 mm, and embedding the outside surface in the longitudinal direction with a resin, leaving the cut ends open. Of course, it is possible to bundle the above number of pieces of hollow fiber membranes obtained by the spinning process and embed the bundle with a resin.

2) The sample is set to a zeta potential analyzer ("EKA" manufactured by Anton Paar GmbH) and a solution obtained by mixing a 0.001 mol/l aqueous solution of potassium chloride and a 0.01 mol/l aqueous solution of potassium hydroxide, and adjusted to pH 10 to 11, is charged from the opening of the bundle of hollow fiber membranes of the sample to measure the zeta potential. Zeta potentials according to the pH change are measured while adding 0.1 mol/l HCl aqueous solution to determine the zeta potential at pH 7.5.

According to the zeta potential measuring method of the present invention, in which the electrolyte is caused to flow through only the inner surface of the hollow fiber membrane and a large and specified number of hollow fibers are used for the measurement, the conditions of the charges on the inner surface of the hollow fiber membrane coming into contact with blood can be evaluated with excellent reproducibility.

In the present invention, the phosphorus-removing performance of the hollow fiber membrane is indicated using the overall mass transfer coefficient of phosphorus. The overall mass transfer coefficient of phosphorus is calculated using an aqueous phosphorus clearance obtained by a clearance measuring method according to a dialyzer performance evaluation standard, in which a module is produced from the hollow fiber membranes using a known method. Specifically, phosphorus concentrations at the inlet and outlet ports of the blood purification apparatus are measured under the conditions of a blood side flow rate of 200 ml/min and a dialysate side flow rate of 500 ml/min, and without filtration, and the measured values are applied to the following equation (1) to calculate the overall mass transfer coefficient (K).

$$CL(\text{ml/min}) = \{(C_{B(in)} - C_{B(out)})/C_{B(in)}\} \times Q_B$$

$$K(\text{cm/min}) = Q_B/\{A \times (1 - Q_B/Q_D)\} \times Ln\{(1 - CL/Q_D)/(1 - CL/Q_B)\} \quad (1)$$

A: Membrane area ($cm^2$)
$Q_B$: Blood side flow rate (ml/min)=200
$Q_D$: Dialysate side flow rate (ml/min)=500
CL: Clearance (ml/min)
$C_{B(in)}$: Phosphorus concentration on the inlet port side of blood purification apparatus
$C_{B(out)}$: Phosphorus concentration on the outlet port side of blood purification apparatus In order to efficiently remove phosphate ions, it is preferable the overall mass transfer coefficient of phosphorus of the hollow fiber membrane is as high as possible. For example, among modules with a comparatively common membrane area of a hemodialyzer of 1.5 $m^2$, a module exceeding a phosphorus clearance of 180 has not been known. This is thus an extremely high clearance which has not been achieved by a conventional blood purification apparatus. The overall mass transfer coefficient calculated using this value is approximately 0.040 cm/min or more. Therefore, in order to obtain an excellent phosphorus removing performance which has not been achieved by a conventional blood purification apparatus, the overall mass transfer coefficient of phosphorus of the hollow fiber membrane is preferably 0.040 cm/min or more. A more preferable overall mass transfer coefficient is 0.045 cm/min or more, at such a level a blood purification apparatus with a membrane area of 1.5 $m^2$ equivalent can exhibit a phosphorus clearance rate of 183.

The hollow fiber membrane for blood purification of the present invention not only has the above-mentioned feature of ameliorating bone metabolism disorder, but also is suitable for ameliorating dialysis amyloidosis and the like. In addition, for more effective improvement of long-term dialysis complications, possession of the following membrane characteristic is extremely preferable. Specifically, said characteristic is excellent capability of fractionating into low-molecular-weight proteins and albumin. The hollow fiber membrane for blood purification having this characteristic is very advantageous, because the membrane can simultaneously remove two or more substances causing the long-term dialysis complications. The fractionability that is concerned with preferred embodiments of the present invention will now be described. In addition, protein adsorption properties, breaking strength, and breaking elongation are also described as the requirements that a hollow fiber membrane is desired to possess from the viewpoint of expression of performance and safety.

The low-molecular-weight protein as used in this invention mainly indicates $\beta_2$-Microglobulin which is a main substance causing the dialysis amyloidosis in long-term dialysis complications, and $\alpha_1$-microglobulin which is not a main substance causing the dialysis amyloidosis but is suspected to be deeply related to the diseases. In addition, other uremic proteins having a molecular weight smaller than albumin and being considered to have involvement in long-term dialysis complications are included as a matter of course.

In the present invention, a sieving coefficient of polyvinylpyrrolidone (hereinafter referred to as PVP) with a weight average molecular weight of 40,000 was used as an index of permeation capability of such low-molecular-weight proteins. Since the sieving coefficient of PVP has a positive correlation to the sieving coefficient of $\beta_2$-microglobulin and the sieving coefficient of $\alpha_1$-microglobulin, this sieving coefficient is effective as a substitute index for simply and stably measuring permeation performance of hollow fiber membranes in an aqueous evaluation system. In addition, the use of the sieving coefficients of $\beta_2$-microglobulin and $\alpha_1$-microglobulin is not practical, because not only measurement of these sieving coefficients in a serum system or plasma system requires a complicated procedure, but also the measured values fluctuate due to variations of protein adsorption amount according to differing serum lots. Although the reason for the variations is not clear, it is thought that mutual actions between the membrane and proteins vary depending on differing serum lots or plasma lots. For these reason, the method of measuring the sieving coefficient of PVP with a weight average molecular weight of 40,000 as an index for measuring the pore size of the hollow fiber membrane was adopt in the present invention.

In the present invention, in order to obtain the permeation performance of low-molecular-weight proteins required for ameliorating long-term dialysis complications, the sieving coefficient of PVP is preferably 45% or more, and more preferably 50% or more.

If the performance of permeating low-molecular-weight proteins is increased by enlarging the average pore size of the hollow fiber membrane as mentioned above, the sieving coefficient of albumin inevitably increases. This is because the number of pores that permit albumin to pass through increases by increasing the average pore size, because there is a certain degree of distribution for the pore size of a hollow fiber membrane. In order to inhibit such an increase in the sieving coefficient of albumin, a conventional technology has adopted a method of increasing selective separation performance of a membrane by enabling multi-layer filtration by increasing the thickness of a dense layer which functions as a selective separation layer in the hollow fiber membrane. However, the studies by the present inventors have revealed that if the thickness of the dense layer is increased, the amount of blood proteins adsorbed to the hollow fiber membrane unexpectedly increases to the extent that such an amount cannot be neglected from the viewpoint of albumin leakage from the living body. This is thought that adsorption of proteins to the hollow fiber membrane is mainly occurred in the dense layer of the hollow fiber membrane. Therefore, in order to solve this problem, it is necessary to maintain the sieving coefficient of albumin at a low level or to reduce the sieving coefficient value, without increasing the thickness of the dense layer of the hollow fiber membrane. In the present invention, a method of sharpening a pore size distribution of a hollow fiber membrane was adopted, that is, a method of increasing fractionability. A specific method for increasing the fractionability by controlling the pore size distribution of hollow fiber membrane will be discussed later as a method for producing the hollow fiber membrane.

A membrane with high fractionability as used in the present invention means a membrane with high permeability of low-molecular-weight proteins, while exhibiting an extremely small albumin removing amount. Here, the albumin removing amount indicates the sum of the total amount of albumin removed from blood by filtration due to the sieving coefficient of albumin and the total amount of albumin lost from blood due to adsorption to the hollow fiber membrane.

Therefore, in order to reduce the amount of albumin removal, it is necessary to reduce the amount of albumin permeating through the membrane by decreasing the sieving coefficient of albumin and to reduce the amount of albumin (proteins) adsorbed to the hollow fiber membrane. For this reason, the sieving coefficient of albumin is preferably 0.6% or less, and more preferably 0.4% or less.

In addition, the rate of proteins adsorbed to hollow fiber membrane should be simultaneously reduced, preferably to 65 mg/m$^2$. A more preferable protein adsorption amount to hollow fiber membrane is 60 mg/m$^2$ or less, with the most preferable amount being 50 mg/m$^2$ or less. In order to reduce the protein adsorption amount to the hollow fiber membrane to 65 mg/m$^2$ or less, the thickness of the dense layer in the hollow fiber membrane is preferably 1 to 5 µm, and more preferably 1 to 3 µm. If the thickness of the dense layer is less than this range, the sieving coefficient of albumin cannot be controlled. If the thickness exceeds this range, the protein adsorption amount to the hollow fiber membrane increases, resulting in an increased loss of proteins.

Another method of reducing the protein adsorption amount to the hollow fiber membrane is to maintain the content of hydrophilic polymers in the hollow fiber membrane in a suitable range. When the content of hydrophilic polymers in the hollow fiber membrane is small, the effect of the hydrophobic polymers forming the basic structure of the membrane is increased, resulting in promoted adsorption of proteins. In particular, in the case of a hollow fiber membrane using PVP as a hydrophilic polymer, if the PVP content is small, protein adsorption is promoted, but if the PVP content in the hollow fiber membrane is large, elution of PVP from the hollow fiber membrane cannot be neglected, and leading to problems such as a decrease of breaking strength and breaking elongation of the membrane. Therefore, the amount of PVP in the hollow fiber membrane is preferably from 3.0 to 5.0 wt %.

In addition, controlling the content of a hydrophilic polymer in this manner is also effective for controlling the zeta potential range of the membrane inner surface. Specifically, if the content of PVP is increased, the zeta potential on the inner surface of membrane tends to also increase, possibly due to gradual masking of hydrophobic polymers resin surface. Therefore, increasing the PVP content is also effective for controlling the phosphorus-removing performance.

As described above, it is important for the hollow fiber membrane for blood purification to control the zeta potential on the inner surface of the membrane, amount of platelet adhesion, overall mass transfer coefficient of phosphorus, sieving coefficient of PVP, sieving coefficient of albumin, and protein adsorption amount to the hollow fiber membrane, all in certain ranges. In addition, breaking strength and breaking elongation should be regarded as important properties to be possessed by the hollow fiber membrane for blood purification. If the breaking strength and breaking elongation are small, defects are easily caused in the hollow fiber membrane, increasing the risk of blood leakage and the like. Therefore, in the hollow fiber membrane for blood purification of the present invention, a breaking strength of 60 kg/cm$^2$ or more and breaking elongation of 60% or more are preferable, with more preferable breaking strength and breaking elongation being 70 kg/cm$^2$ or more and 65% or more, respectively.

There has not been known any hollow fiber membrane for blood purification that satisfies the conditions of a zeta potential of greater than –3.0 mV but less than 0 mV and the above-described fractionability and protein adsorption amount, and these requirements for breaking strength and breaking elongation.

Figure 1:
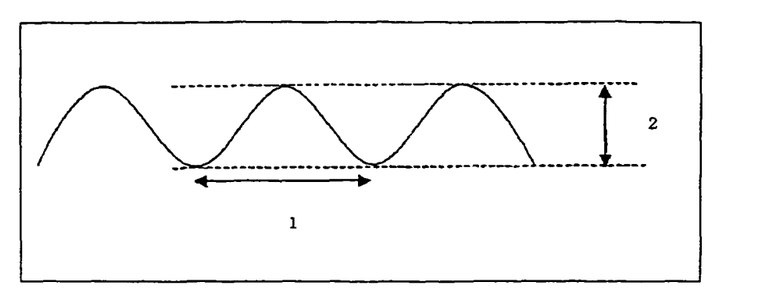
FIG. 1 is a schematic drawing showing a crimp form of the hollow fiber membrane of the present invention.

There are no specific limitations to the form of the hollow fiber membrane. Although the hollow fiber may be a straight yarn, a hollow fiber with crimps is more preferable from the viewpoint of the diffusion efficiency during hemodialysis. The form of the crimps is specified by the wavelength and amplitude, those are defined as shown in FIG. 1, respectively. The wavelength is preferably from 2 mm to 20 mm, and more preferably from 4 mm to 8 mm. The amplitude is preferably from 0.1 mm to 5 mm, and more preferably from 0.2 mm to 1 mm.

Next, a method for producing the hollow fiber membrane for blood purification of the present invention will be specifically described.

The method for producing the hollow fiber membrane for blood purification of the present invention comprises at least a step of extruding a raw spinning solution containing a hydrophobic polymer, a hydrophilic polymer, and a solvent from a spinneret together with a hollow-making inner solution, a step of coagulating the extruded raw spinning solution, and a step of drying the coagulated hollow fiber membrane. A commonly known dry-and-wet membrane-forming technology can be applied.

Almost all engineering plastics such as a polysulfone-based resin, polyether sulfone-based resin, polyamide-based resin, polyimide-based resin, polyphenyl ether-based resin, polyphenylene sulfide-based resin and the like can be used as the hydrophobic polymer in the present invention. The pore size of membranes made from these engineering plastics can be easily controlled, if these engineering plastics are blended with the hydrophilic polymers described below. These engineering plastics are thus particularly suitable for obtaining a hollow fiber membrane with the permeability range targeted in the present invention. Here, the term "-based resin" indicates the resins including those having a typical structure, as well as those in which the structure is partly altered or modified. Among these resins, the polysulfone-based resin (hereinafter abbreviated as "PSf") is particularly preferably used due to the excellent biocompatibility, biological safety, durability, and the like and abundant use experience as a hollow fiber membrane for blood purification.

As the hydrophilic polymer of the present invention, polyvinylpyrrolidone, polyethylene glycol, polyglycol monoester, starch, and their derivatives, and water-soluble cellulose derivatives such as carboxymethylcellulose and cellulose acetate can be used. It is also possible for these hydrophilic polymers to use in combination. From the viewpoint of spinning stability and affinity with PSf, polyvinylpyrrolidone and polyethylene glycol are preferably used, with polyvinylpyrrolidone is most preferable. Polyvinylpyrrolidone (hereinafter abbreviated as "PVP") is a water-soluble polymer produced by vinyl polymerization of N-vinylpyrrolidone. Several PVPs with different molecular weights are commercially available under the brand names of "Plasdone (trademark)" (manufactured by ISP Chemicals Corp.) and "Kollidon (trademark)" (manufactured by BASF).

These hydrophilic polymers are deposited on the surface of the hydrophobic polymer resin during the coagulation step in the dry-and-wet spinning process and hydrophilize the resin surface, thereby promoting the antithrombogenicity. In addition, the hydrophilic polymers are thought to change the zeta potential on the inner surface of the membrane according to the difference of deposition amount and deposition state.

As the membrane-forming raw spinning solution for the dry-and-wet membrane-forming process, a solution of a polysulfone-based resin and polyvinylpyrrolidone dissolved in a solvent which can dissolve both the polysulfone-based resin and polyvinylpyrrolidone can be used. Although said solvent is not specifically limited, as examples, solvents such as dimethyl acetamide (hereinafter abbreviated as "DMAC"), dimethyl sulfoxide, N-methyl-2-pyrrolidone, dimethylformamide, sulfolane, and dioxane, and mixed solvents of two or more of these solvents can be given. DMAC is preferable from the viewpoint of solubility to polysulfone, biological safety, cost, and the like. Additives such as water may be added to the raw spinning solution to control the pore size.

Next, using a tube-in-orifice-type spinneret, a raw spinning solution and a hollow-making inner solution for coagulating the raw spinning solution are simultaneously extruded respectively from the orifice and tube of the spinneret into the air. Water or a coagulating solution of which the main component is water can be used as the hollow-making inner solution. In general, a mixed solution of the solvent used for raw spinning solution and water is preferably used. For example, an aqueous solution of 0 to 60 wt % DMAC is used. The raw spinning solution extruded from the spinneret together with the hollow-making inner solution runs through air gap, is introduced into a coagulation bath containing water as a main component installed below the spinneret, and dipped in the coagulation bath to complete the coagulation. After dipping in the coagulation bath and a refining step, the hollow fiber membrane is introduced into a dryer and dried there, followed by winding to obtain a product of hollow fiber membrane. In this instance, crimping the hollow fiber membrane is preferable for the membrane to efficiently exhibit diffusion performance when used for hemodialysis. It is also possible to dry the hollow fiber membrane after cutting the membranes in the wet state and bundling.

In order to express the zeta potential on the inner surface in the hollow fiber membrane of the present invention, it is important to control the membrane forming conditions in the process from membrane-forming, extrusion of the raw spinning solution to be coagulated from a spinneret, to the coagulating bath. In particular, control of the running time and relative humidity of the air gap in the dry-and-wet spinning, and control of subsequent coagulation conditions are important. It is preferable for the membrane-forming raw spinning solution to be appropriately coagulated during the period from being extruded from the spinneret to being dipped in the coagulating bath. To this end, the running time in the air gap is preferably 0.4 seconds or more, and more preferably 0.5 seconds or more. The running time through the air gap can be controlled by the spinning rate. If the running time through the air gap is 0.1 second or less, the hollow fiber membrane is dipped in the coagulating bath in an inadequate coagulated state. This increases the amount of water-soluble polyvinylpyrrolidone eluted into the coagulate bath and reduces the amount of polyvinylpyrrolidone remaining in the hollow fiber membrane, giving rise to insufficient hydrophilization. It is unpreferably difficult for such a hollow fiber membrane of the present invention to express the zeta potential on the inner membrane surface. The upper limit of running time varies according to the running distance in the air gap. When the running distance is 50 cm, a running time not exceeding 2.0 seconds is preferable.

Humidity in the air gap is another important condition. The relative humidity in the air gap is preferably 70 to 95%, and more preferably 75 to 90%. If the relative humidity is low, there may be cases in which a hollow fiber membrane cannot be sufficiently formed before being dipped in the coagulating bath, an appropriate membrane structure that can control the zeta potential on the inner surface of the membrane of the present invention cannot be formed, and hollow fiber membranes become attached to one another, leading to unstable spinning. In contrast, if the relative humidity is too high, coagulation of the raw spinning solution on the outer surface is promoted to reduce the pore diameter of the hollow fiber membrane. This results in an increase of permeation/diffusion resistance during blood purification and a poor solute removal efficiency unpreferably. In the present invention, the air gap means the entire region from the spinneret to the coagulation bath through which the hollow fiber membrane is transferred.

Although the method for producing a hollow fiber membrane with a controlled zeta potential on the inner surface of the membrane is as described above, in order to obtain a hollow fiber membrane which can more effectively ameliorate a long-term dialysis complication, it is important to increase the capability of fractionating into low-molecular-weight proteins and albumin, for example. According to the finding of the present inventors, in order to produce a hollow fiber membrane with excellent fractionability so that a PVP sieving coefficient is 45% or more and an albumin sieving coefficient is 0.6% or less, the pore size of the hollow fiber membrane before drying (in a wet state) must be reduced. This is because the inadequate structural change which a hollow fiber membrane in a wet state undergoes by drying leads to leakage of albumin from the hollow fiber membrane. Therefore, the PVP sieving coefficient of the hollow fiber membrane before drying is preferably 95% or less, and more preferably 90% or less. In this manner, the structural change before and after drying of the hollow fiber membrane, in other words, the structural shrinkage occurring when the membrane in a wet state is dried, must be controlled to the minimum. To this end, in addition to a later-described method, a method of increasing breaking strength and breaking elongation of the hollow fiber membrane by retarding the spinning speed or increasing the polymer concentration of the raw spinning solution can be given.

A first method for reducing a structural shrinkage is preferably to increase the coagulation bath temperature to 80° C. or more, more preferably 85° C. or more, and still more preferably 90° C. or more. Although the mechanism is still to be elucidated, because a high coagulation bath temperature during the spinning operation increases pore diameter of the hollow fiber membrane, the solvent concentration of the hollow-making inner solution must be reduced to control the average pore diameter. A reduced solvent concentration of the hollow-making inner solution increases the coagulation force of the hollow-making agent and can produce a stronger dense layer in the air gap. This is thought to be a mechanism for reducing the structural shrinkage. On the other hand, because too high a coagulation bath temperature unduly impairs workability, the temperature should preferably be 100° C. or less.

Another important factor for reducing the structural shrinkage is the solvent (DMAC) gas concentration in the air gap. The structure of the hollow fiber membrane is formed by phase separation during running in the air gap after being extruded from the spinnerets. It has been newly found that the structure formation is greatly affected by not only temperature and humidity, but also by the solvent gas concentration in the air gap. If the solvent gas concentration in the air gap is small, the structural shrinkage tends to increase. This tendency is remarkably noted when the air of which the temperature and humidity are controlled by an air processor or the like is introduced into the air gap. Although the reason for this phenomenon is not clear, promoted vaporization of the solvent from the outside surface of the fiber in the air gap allows the fiber with a high polymer concentration on the outer surface to enter the coagulation bath, which is thought to increase a shrinkage force.

On the other hand, in the case in which a solvent gas is introduced into the air gap, the structural shrinkage reduces. The reason is thought to be because an increased thickness of the gas diffusion layer near the outer surface of the fiber reduces the amount of the solvent gas vaporized from the fiber, which reduces shrinkage in the coagulation bath. An optimal solvent gas concentration in the air gap is 150 ppm or more and 1,000 ppm or less. It is difficult to inhibit the structural shrinkage if the concentration is less than 150 ppm; whereas a concentration of 1,000 ppm or more worsens the working environment and has a problem of providing a non-coagulated outer surface of the fiber. The solvent gas concentration can be measured using a gas-detecting tube, gas detector, gas chromatography, and the like. Measurement using a gas-detecting tube is easy and preferable.

As the methods for maintaining the solvent concentration in the air gap in this range, a method of sealing the air gap and introducing the solvent gas therein, a method of increasing the solvent concentration in the coagulation bath, a method of supplying a solvent to the hood of the air gap, and the like can be given. Any method can be used either individually or in combination. The hood of the air gap here refers to an enclosure of the air gap.

In order to set the thickness of the dense layer of the hollow fiber membrane in an appropriate range for reducing the protein adsorption amount to the hollow fiber membrane, the composition of the hollow-making inner solution, viscosity of the raw spinning solution, temperature of the raw spinning solution during extrusion, and the like must be appropriately determined. For example, if the amount of poor solvent to PSf in the hollow-making inner solution is small, the coagulation force is reduced and coagulation mildly proceeds, whereby the dense layer is provided with a rough and thick structure. On the other hand, if the amount of poor solvent to PSf in the hollow-making inner solution is great, the dense layer is provided with a dense and thin structure. When the viscosity of the raw spinning solution is high, transfer of a polysulfone-based polymer is suppressed during coagulation, whereby the thickness of the dense layer is increased as compared with the case in which the viscosity is low otherwise under the same conditions. When the temperature of the raw spinning solution during extrusion is high, transfer of PSf is contrary accelerated during coagulation, whereby the thickness of the dense layer is reduced as compared with the case in which the temperature of the raw spinning solution is low otherwise under the same conditions. The thickness of the dense layer is also affected by a spinning draft conditions, the distance of the air gap from spinneret to the coagulation bath, the size of the spinneret, spinning speed, and the like. These conditions and combination of conditions must be set taking into account the permeation performance of the membrane, breaking strength and breaking elongation, the object, and the like.

In addition, in order to set the concentration of PVP in the hollow fiber membrane in an appropriate range for reducing the protein adsorption amount to the hollow fiber membrane, the mixing ratio of PVP to PSf in the raw spinning solution is preferably set to 0.2 to 0.5.

In order to increase the breaking strength and breaking elongation of a hollow fiber membrane, tension applied to one piece of hollow fiber membrane throughout the membrane-forming process must be reduced. Usually, the breaking strength and breaking elongation of the hollow fiber membrane decrease as the pore diameter increases. This is attributed to the increase in the porosity of the hollow fiber membrane. In the present invention, the tension applied to one piece of the hollow fiber membrane throughout the entire process from spinning to drying is decreased by reducing fluctuation of tension, and employing an apparatus for winding the membrane at a constant tension and other means. As a result, it was found that a hollow fiber membrane with sufficiently high breaking strength and breaking elongation in spite of a large pore diameter can be obtained. At that time, the maximum tension applied to one piece of the hollow fiber membrane throughout the entire process from spinning to drying is preferably less than 2.5 g, and more preferably 0.1 to 2.5 g. Although the reason is not clear, it is thought that the breaking strength and breaking elongation might decrease in the prior art technique due to drawing of the hollow fiber membrane during the process. It is presumed that the smaller the tension during the process, the greater the chance for polymers in the membrane to bond together closely, resulting in an increase in the breaking strength and breaking elongation even if the porosity remains the same.

The method for crimping the hollow fiber membrane includes, but is not limited to, a method of producing crimps by continuously forwarding the hollow fiber membrane into the clearance between two rolling gears to replicate the configuration of gears and a method of providing the hollow fiber membrane with a crimped configuration by subjecting the hollow fiber membrane wound onto a bobbin to a heat treatment.

The blood purification apparatus of the present invention can be obtained by fabricating a module from the hollow fiber membrane of the present invention with reference to a known method described in Japanese Patent Application Laid-open No. 11-90186 or Japanese Patent Application Laid-open No. 2003-265934, for example.

Specifically, hollow fiber bundle, bundling several hundreds to several tens of thousands of hollow fiber membranes, is loaded in a plastic cylindrical container with two nozzles for flowing dialysate therethrough near both ends. Then, a potting material of a curable resin such as a polyurethane resin is applied to both ends. The hollow fiber bundle is secured to the inner surface of the cylindrical container when the potting resin is cured. The cured resin is cut to form openings in the hollow fiber membranes at both ends. A module structure with the hollow internal part and the hollow external part separated by a partition at both ends of the cylindrical container can be obtained in this manner. Header caps having nozzles for flowing blood therethrough are attached to both ends of the module and the resulting module is sterilized to obtain a blood purification apparatus.

For blood purification, the blood is flowed through the inside of the hollow fiber membrane, while a dialysate containing an electrolyte and the like is flowed along the outside thereof. Filtration pressure is applied by controlling the flow rates of pumps on the blood side and/or the dialysate side or by another means to cause waste materials and harmful substances in the blood to be diffused in the dialysate side and removed according to the principle of filtration.

EXAMPLES

The present invention is described below in detail by way of examples and comparative examples. However, the present invention is not limited to such examples.
(Measurement of Phosphorus Clearance)

A module as a blood purification apparatus with a prescribed membrane area was prepared from the hollow fiber membrane and the phosphorus clearance was measured according to the dialyzer performance evaluation standard (edited by Japanese Society for Artificial Organs; September, 1982). Commercial blood purification apparatus is measured as is.

A 5 mEq/l inorganic phosphorus physiological saline solution (an aqueous solution mixed aqueous solutions of 5 mEq/l monosodium phosphate and 5 mEq/l disodium phosphate in a ratio of 1:4, adjusted to pH 7.4) was circulated through the blood side at a flow rate of 200 ml/min, while circulating a physiological saline solution through the dialysate side at a rate of 500 ml/min, thus dialysis is conducted under conditions wherein filtration does not occur. The circulating fluids were sampled from the blood inlet side and outlet side. The phosphorus concentration in the sample solutions were measured by the molybdenum blue coloring method and the phosphorus clearance was calculated using the following equation (2). In the test, the blood purification apparatus in a dry state was used for measurement after 60 minutes or more following a wetting treatment.

$$\text{Phosphorus clearance (ml/min)} = \{(C_{B(in)} - C_{B(out)})/C_{B(in)}\} \times Q_B \quad (2)$$

$C_{B(in)}$: Phosphorus concentration on the inlet port side of the blood purification apparatus
$C_{B(out)}$: Phosphorus concentration on the outlet port side of the blood purification apparatus
$Q_B$: Flow rate on the blood side (ml/min)=200
(Measurement of Antithrombogenicity)

The antithrombogenicity employs the amount of platelet adhered to the inner surface of a hollow fiber membrane as an index and can be determined by measuring in vitro lactate-dehydrogenase (LDH) activity in platelets. The strong correlation between the number of platelets and LDH activity enables the measurement of the number of adhered platelets by LDH activity.

Specifically, it can be carried out by the following method.
1) Fabricate a miniature module of 60 filaments×15 cm.
2) Wash the miniature module by flowing 25 ml of a physiological saline solution therethrough.
3) Flow a human blood to which heparin is added through the miniature module at a blood linear velocity of 1.25 cm/second for five minutes, followed by washing with a physiological saline solution.
4) After washing, remove the hollow fiber membranes from the miniature module, cut the hollow fiber membranes fine, and elute LDH from platelets in 0.5 wt % Triton-X (Kishida Chemical Co., Ltd.)/PBS (−) (Dulbecco-modified medium, manufactured by Nissui Pharmaceutical, Co., Ltd.) solution.
5) As LDH produces lactic acid when pyruvic acid is used as a substrate in the presence of β-Nicotinamide adenine dinucleotide reduced form (β-NADH; N8129, manufactured by SIGMA Co.), the rate of NADH is measured from the change of absorbance to calculate the LDH activity, which is converted into the number of platelets.

Although the details are omitted, the number of platelets adhering to the inner surface of the hollow fiber membranes can also be confirmed by direct counting or image analysis determination by observing the inner surface of the hollow fiber membrane using a scanning electron microscope.
(Sieving Coefficient of PVP)

Hollow fiber membranes were sampled and a miniature module with an effective length of 18 cm was fabricated. Hollow fiber membranes either in a wet condition or dry condition can be used for fabrication of the miniature module. A 3 wt % aqueous solution of PVP ("K-30" manufactured by ISP) with a weight average molecular weight of about 40,000 dissolved in a 1/15 mol/l phosphate buffer solution was flowed through the miniature module and filtered by a flow method under the condition of a trance membrane pressure of 200 mmHg, a linear velocity of 1 cm/sec, and a temperature of 25° C. The value calculated from the original solution and filtrate according to the following equation (3) at that time is defined as the sieving coefficient of PVP.

$$\text{Sieving coefficient of } PVP = (PVP \text{ concentration of filtrate})/(PVP \text{ concentration of original solution}) \times 100(\%) \quad (3)$$

The filtrate was sampled for five minutes, from 20 minutes to 25 minutes after beginning of the filtration.
(Sieving Coefficient of Albumin)

Bovine serum as an original solution, of which the total protein concentration was adjusted to 6.5 g/dl by adding a physiological saline solution, was flowed through the miniature module at a linear velocity of 0.4 cm/sec and a trance membrane pressure of 25 mmHg, to collect filtrate. The temperatures of the original solution and the measuring circumstance were 25° C. Hollow fiber membranes constituting the miniature module may be either in a wet condition or dry condition. The albumin concentration was then determined by the BCG method and a value calculated from the following equation (4) is defined as the sieving coefficient of albumin.

$$\text{Sieving coefficient of albumin} = (\text{Albumin concentration of filtrate})/(\text{Albumin concentration of original solution}) \times 100(\%) \quad (4)$$

Here, as the sieving coefficient the value obtained after 60 minutes from the beginning of the filtration was used.
(Protein Adsorption Amount)

The protein adsorption amount to the hollow fiber membranes was measured using the miniature module after measuring the sieving coefficient of albumin.

150 filaments of 14 cm hollow fiber membranes were extracted from the miniature module, cut into 2 to 3 mm length, and placed in a sample bottle. In order to wash the bovine serum contained in the hollow portion and membrane thickness portion of the hollow fiber membranes, a physiological saline solution was put into the sample bottle, allowed to stand for 30 minutes, and discharged. This procedure was repeated three times to complete washing. 5 ml of a solution (SDS solution) prepared by adding 1 wt % sodium laurylsulfate to a 0.1 mol/l phosphate buffer solution was added to the sample bottle containing the washed hollow fiber membranes and stirred for four hours to release proteins adsorbed to the hollow fiber membranes. After stirring, the concentration of proteins in the SDS solution was determined by the BCG method and the protein adsorption amount to the hollow fiber membrane was calculated using the following equation (5).

Protein adsorption amount to hollow fiber membrane=(Amount of proteins released in SDS solution)/(Total of inner surface area of hollow fiber membranes contained in the used miniature module) (5)

(Thickness of Dense Layer)

A cross-section image of a hollow fiber membrane obtained by a transmission electron microscope was partitioned along the direction of the cross-section into compartments with a prescribed constant width. Each compartment was subjected to image analysis to determine the proportion (composition ratio) of the space occupied by the polymer. The distribution or change of the composition ratio in the cross-section direction of the hollow fiber membrane could be quantitatively determined by repeating the image analysis from the inner side toward the outer side of the hollow fiber membrane. In the present invention, when image-analyzing the hollow fiber membrane by a image-analyzing width of 0.5 µm to 1.0 µm, the area occupied from the compartment with the highest composition ratio to the compartment within 30% of composition ratio was defined as the dense layer and its thickness was measured.

(PVP Content in the Hollow Fiber Membrane)

0.1 g of hollow fiber membranes dried in advance was completely dissolved in 2 ml of N-methyl-2-pyrrolidone. 99 ml of distilled water for injection at 55° C. was added to the solution and the mixture was stirred to extract PVP in the distilled water for injection. PVP in this aqueous solution was quantitatively analyzed by GPC (gel permeation chromatography). Prior to the test, PSf and PVP used as the raw materials for the hollow fiber membranes to be measured were mixed at a prescribed ratio. After carrying out the same procedure as above, the correlation between the mixing ratio of PSf/PVP and the peak area of PVP by GPC was obtained to prepare a calibration curve. The content of PVP in the hollow fiber membranes was calculated using this calibration curve.

(Breaking Strength and Breaking Elongation)

One piece of dry hollow fiber membrane was secured by chuck parts of a tensile tester (EZ Test series, manufactured by Shimadzu Corp.). At that time, the length of the hollow fiber membrane was 20 cm. When the obtained hollow fiber membrane was in a wet condition, the hollow fiber membrane was dried at about 90° C. using a hot air drier prior to the measurement. The hollow fiber membrane was drawn at a rate of 30 cm/min to measure the breaking strength and breaking elongation when the hollow fiber membrane was broken. The strength when the hollow fiber membrane was broken was divided by the cross-section area of the hollow fiber membrane, and the obtained value was defined as the breaking strength, and the breaking elongation when the hollow fiber membrane was broken was divided by the length (20 cm) of the hollow fiber membrane before measurement, and the obtained value was defined as the elongation.

Example 1

A homogeneous raw spinning solution consisting of 17 parts by weight of PSf ("P-1700" manufactured by Solvay Advanced Polymers, K. K.), 4 parts by weight of PVP ("K-90" manufactured by ISP Chemicals Corp.), and 79 parts by weight of dimethylacetamide (hereinafter abbreviated as "DMAC") was prepared. Using 41 wt % aqueous solution of DMAC as a hollow-making inner solution, the raw spinning solution was extruded from spinnerets with a slit width of 50 µm. At that time, the temperature of the raw spinning solution during extrusion was 60° C. The air gap was covered with a hood to make the relative humidity to 95%. In addition, DMAC gas was introduced to adjust the DMAC gas concentration of the air gap to 470 ppm. The hollow fiber membrane was dipped in a coagulation bath of water at 90° C. installed at a location of 50 cm below the spinnerets, caused to pass through a refining bath and a dryer controlled at 160° C., and wound up. At that time, the spinning speed was set to 30 m/min to provide a one second running time through the air gap. The maximum tension applied to the hollow fiber membrane during the membrane forming process was 2.3 g. The extrusion amounts of the raw spinning solution and hollow-making inner solution were controlled so as to make the membrane thickness after drying 45 µm and the inner diameter 200 µm. The resulting hollow fiber membrane was loaded in a container to provide a packed membrane area of 1.5 m$^2$, and followed by making a module by potting. A blood purification apparatus was obtained by irradiating with γ-rays in a wet state.

The phosphorus clearance was measured using this blood purification apparatus. An overall mass transfer coefficient (K) was calculated from the resulting value. Thereafter, the blood purification apparatus was disassembled and taken out the hollow fiber membrane to measure the zeta potential at pH 7.5, amount of platelet adhesion, sieving coefficient of PVP, sieving coefficient of albumin, protein adsorption amount to the membrane, breaking strength, breaking elongation, thickness of dense layer, and PVP content in the membrane. The K value of PVP used for measuring the sieving coefficient of PVP was 30.5.

The operating conditions and measuring results of this and other examples and comparative examples are shown in Tables 1 and 2.

Example 2

A homogeneous raw spinning solution consisting of 18 parts by weight of PSf ("P-1700" manufactured by Solvay Advanced Polymers, K. K.), 7 parts by weight of PVP ("K-90" manufactured by ISP Chemicals Corp.), and 75 parts by weight of dimethylacetamide (hereinafter abbreviated as "DMAC") was prepared. Using a 44% aqueous solution of DMAC as a hollow-making inner solution, the raw spinning solution was extruded from spinnerets with a slit width of 50 µm. The air gap was covered with a hood to make the relative humidity to 70%. In addition, DMAC gas was introduced to adjust the DMAC gas concentration of the air gap to 870 ppm. Then, the same procedure as in Example 1 was followed to obtain a blood purification apparatus.

Example 3

A homogeneous raw spinning solution consisting of 16 parts by weight of PSf ("P-1700" manufactured by Solvay Advanced Polymers, K. K.), 3.5 parts by weight of PVP ("K-90" manufactured by ISP Chemicals Corp.), and 81.5 parts by weight of dimethylacetamide (hereinafter abbreviated as "DMAC") was prepared. Using a 46% aqueous solution of DMAC as a hollow-making inner solution, the raw spinning solution was extruded from spinnerets with a slit width of 50 µm. The air gap was covered with a hood to make the relative humidity to 90%. In addition, DMAC gas was introduced to adjust the DMAC gas concentration of the air gap to 270 ppm. Then, the same procedure as in Example 1 was followed to obtain a blood purification apparatus.

Example 4

A blood purification apparatus was obtained in the same manner as in Example 1, except that the spinning speed was set to 60 m/min to provide a running time of 0.5 second in the air gap.

Example 5

A blood purification apparatus was obtained in the same manner as in Example 3, except that the coagulating bath temperature was 75° C.

Example 6

A blood purification apparatus was obtained in the same manner as in Example 1, except that DMAC gas was not introduced and the DMAC gas concentration in the air gap was controlled to 90 ppm.

Example 7

A blood purification apparatus was obtained in the same manner as in Example 1, except that 21 parts by weight of PSf ("P-1700" manufactured by Solvay Advanced Polymers, K. K.), 3 parts by weight of PVP ("K-90" manufactured by ISP Chemicals Corp.), and 79 parts by weight of dimethylacetamide (hereinafter abbreviated as "DMAC") were used.

Example 8

A blood purification apparatus was obtained in the same manner as in Example 1, except that the maximum tension applied to the hollow fiber membrane during the membrane forming process was 2.8 g.

Results of the Examples

The hollow fiber membranes obtained in Examples 1-4 were proven to exhibit excellent phosphorus-removing performance, while maintaining antithrombogenicity, in addition removing performance superior in fractionability of inhibiting leakage of a useful protein of albumin, while showing high performance removing low-molecular-weight proteins, and excellent safety with a minimal risk of blood leakage. The hollow fiber membranes obtained in Examples 5 and 6 exhibited a slightly higher albumin permeation rate as compared with those of Examples 1-4. The hollow fiber membrane obtained in Example 7 exhibited a high protein adsorption amount. The hollow fiber membrane obtained in Example 8 exhibited low breaking strength and breaking elongation. All of these hollow fiber membranes were proven to exhibit excellent phosphorus-removing performance, while maintaining antithrombogenicity.

From the above results of the examples, it can be understood that a hollow fiber membrane with excellent capability of separating low molecular weight proteins and albumin can be obtained by setting the coagulation bath temperature or the solvent concentration in the air gap to a desired range, in the manufacture conditions for obtaining the zeta potential on the inner surface of the hollow fiber membrane of the present invention. In addition, it can be understood that protein adsorption to the membrane is inhibited by setting the mixing ratio of PVP to PSf in the raw spinning solution in a desired range, and a hollow fiber membrane with excellent breaking strength and breaking elongation can be obtained by setting a tension in a desired range. The hollow fiber membrane of the present invention obtained in the manner as mentioned above is useful for not only improving bone metabolism disorders by removing phosphorus, but also ameliorating dialysis amyloidosis by further controlling the production conditions. Therefore, the hollow fiber membrane possesses characteristics suitable for more effectively improving long-term dialysis complications.

In addition, the blood purification apparatus of the present invention, in which such a hollow fiber membrane is used, exhibited superior phosphorus-removing performance.

Comparative Example 1

A blood purification apparatus was obtained in the same manner as in Example 4, except that the spinning speed was set to 80 m/min to provide a running time of 0.3 second in the air gap.

The resulting hollow fiber membrane exhibited a strong negative charge of a −4.8 mV zeta potential on the inner surface at pH 7.5 and a small overall mass transfer coefficient of phosphorus.

Comparative Example 2

A blood purification apparatus was obtained in the same manner as in Example 1, except that the relative humidity in the air gap was 60%. The resulting hollow fiber membrane exhibited a strong negative charge of a −3.3 mV zeta potential on the inner surface at pH 7.5 and a small overall mass transfer coefficient of phosphorus.

Comparative Example 3

A homogeneous raw spinning solution consisting of 18 parts by weight of PSf ("P-1700" manufactured by Solvay Advanced Polymers, K. K.), 4.8 parts by weight of PVP ("K-90" manufactured by BASF), and 77.2 parts by weight of dimethylacetamide (hereinafter abbreviated as "DMAC") was prepared. Using a 52 wt % aqueous solution of DMAC as a hollow-making inner solution, the raw spinning solution was extruded from spinnerets with a slit width of 50 µm. At that time, the extrusion temperature of the raw spinning solution was 60° C. In addition, the air gap was enclosed with a hood and the relative humidity and temperature in the hood was controlled at 54.5% and 51° C., respectively, by flowing nitrogen gas containing steam therethrough. The DMAC gas concentration in the air gap was 30 ppm at that time. The hollow fiber membrane was dipped in a coagulation bath of water at 75° C. installed at a location of 96 cm below the spinnerets, and wound up. At that time, the spinning speed was 80 m/min. After cutting the wound fiber, the fibers were washed by showering 80° C. hot water for 2 hours from the upper cut surface of the bundle to remove the remaining solvent in the membranes. These membranes were further dried using hot air at 87° C. for 7 hours to obtain hollow fiber membranes. Then, a blood purification apparatus was obtained in the same manner as in Example 1 as follows.

The resulting hollow fiber membrane exhibited a strong negative charge of a −5.2 mV zeta potential at pH 7.5 on the inner surface and a small overall mass transfer coefficient of phosphorus.

Comparative Example 4

The hood covering the air gap was sealed, DMAC was added to a glass container to vaporize in the hood, and the DMAC concentration was adjusted to 1,500 ppm in the hood. A hollow fiber membrane was obtained in the same manner as in Example 1, except that the location of the glass container was adjusted so that the hollow fiber membrane can be directly dipped in the coagulation bath.

The resulting hollow tended to easily attach to one another and the hollow was squashed or crushed with the probability of about 50% during the drying operation. Therefore, the product was not evaluated. The outer surface of the hollow fiber membrane was observed using a scanning electron microscope to confirm that the pore size was small and the number of pore was also poor. As the concentration of DMAC in the hood of the air gap was too high, it is thought to have adversely affected the formation of the outer surface structure of the membrane.

Comparative Example 5

The evaluation experiment was carried out in the same manner as in Example 1, except for using a blood purification apparatus made of polysulfone ("F80S" manufactured by Fresenius Co., Lot No. CCC121). The hollow fiber membrane exhibited a strong negative charge of a −3.9 mV zeta potential at pH 7.5 on the inner surface and a small overall mass transfer coefficient of phosphorus.

Comparative Example 6

The evaluation experiment was carried out in the same manner as in Example 1, except for using a blood purification apparatus made of polyether sulfone ("PES-150D" manufactured by NIPRO Corp., Lot No. 02D29). The hollow fiber membrane exhibited a strong negative charge of a −10.6 mV zeta potential at pH 7.5 on the inner surface and a small overall mass transfer coefficient of phosphorus.

Comparative Example 7

The evaluation experiment was carried out in the same manner as in Example 1, except for using an artificial kidney made of polysulfone ("APS-150U" manufactured by Asahi Medical Co., Ltd., Lot No. L37L7U-T). The hollow fiber membrane exhibited a strong negative charge of a −6.67 mV zeta potential at pH 7.5 on the inner surface and a small overall mass transfer coefficient of phosphorus.

TABLE 1

| | Example | | | | | | | | Comparative Example | | | | | | |
|---|---|---|---|---|---|---|---|---|---|---|---|---|---|---|---|
| | 1 | 2 | 3 | 4 | 5 | 6 | 7 | 8 | 1 | 2 | 3 | 4 | 5 | 6 | 7 |
| Relative humidity in air gap (%) | 95.0 | 70.0 | 90.0 | 95.0 | 90.0 | 95.0 | 95.0 | 95.0 | 95.0 | 60.0 | 54.5 | 95.0 | — | — | — |
| Running time through air gap (sec) | 1.0 | 1.0 | 1.0 | 0.5 | 1.0 | 1.0 | 1.0 | 1.0 | 0.3 | 0.8 | 0.7 | 1.0 | — | — | — |
| Coagulation bath temperature (° C.) | 90 | 90 | 90 | 90 | 75 | 90 | 90 | 90 | 90 | 90 | 75 | 90 | — | — | — |
| Solvent concentration in air gap (ppm) | 470 | 870 | 270 | 470 | 270 | 90 | 470 | 470 | 470 | 470 | 30 | 1.500 | — | — | — |
| PVP/PSf ratio in raw spinning solution (—) | 0.24 | 0.39 | 0.22 | 0.24 | 0.22 | 0.24 | 0.14 | 0.24 | 0.24 | 0.24 | 0.22 | 0.24 | — | — | — |
| Tension applied in air gap (g) | 2.3 | 2.3 | 2.3 | 2.3 | 2.3 | 2.3 | 2.3 | 2.8 | 2.3 | 2.3 | 2.3 | 2.3 | — | — | — |

TABLE 2

| | Example | | | | | | | |
|---|---|---|---|---|---|---|---|---|
| | 1 | 2 | 3 | 4 | 5 | 6 | 7 | 8 |
| Zeta potential on inner surface of membrane (mV) | −0.20 | −0.18 | −0.25 | −2.70 | −0.20 | −0.23 | −0.13 | −0.10 |
| Overall mass transfer coefficient of phosphorus (cm/min) | 0.042 | 0.045 | 0.042 | 0.041 | 0.041 | 0.041 | 0.042 | 0.043 |
| Number of attached platelets ($10^3/cm^2$) | 6.3 | 6.4 | 6.6 | 6.2 | 6.6 | 6.5 | 7.2 | 6.8 |
| Sieving coefficient of PVP (%) | 50.2 | 49.0 | 68.4 | 53.2 | 45.8 | 47.2 | 45.0 | 53.1 |
| Sieving coefficient of albumin (%) | 0.18 | 0.14 | 0.55 | 0.35 | 0.62 | 0.68 | 0.22 | 0.24 |
| Protein adsorption amount (mg/m²) | 29 | 58 | 22 | 36 | 30 | 45 | 89 | 34 |

TABLE 2-continued

| | | | | | | | |
|---|---|---|---|---|---|---|---|
| Breaking strength (kg/cm²) | 71.0 | 69.5 | 62.7 | 70.0 | 66.2 | 68.8 | 79.3 | 57.8 |
| Breaking elongation (%) | 70 | 69 | 64 | 63 | 65 | 71 | 65 | 56 |
| Thickness of dense layer (μm) | 3.0 | 4.5 | 1.5 | 3.5 | 1.5 | 3.0 | 3.0 | 3.0 |
| PVP content in membrane (%) | 3.8 | 4.7 | 3.5 | 3.2 | 3.7 | 3.8 | 2.7 | 4.0 |
| Phosphorus clearance (ml/min) | 181 | 183 | 181 | 180 | 180 | 180 | 181 | 182 |

| | Comparative Example | | | | | | |
|---|---|---|---|---|---|---|---|
| | 1 | 2 | 3 | 4* | 5 | 6 | 7 |
| Zeta potential on inner surface of membrane (mV) | −4.80 | −3.30 | −5.20 | — | −3.90 | −10.60 | −6.67 |
| Overall mass transfer coefficient of phosphorus (cm/min) | 0.031 | 0.036 | 0.034 | — | 0.038 | 0.031 | 0.034 |
| Number of attached platelets (10³/cm²) | 6.5 | 6.7 | 6.0 | — | 6.7 | 6.4 | 6.0 |
| Sieving coefficient of PVP (%) | 55.1 | 53.4 | 70.5 | — | — | — | — |
| Sieving coefficient of albumin (%) | 0.44 | 0.20 | 0.72 | — | — | — | — |
| Protein adsorption amount (mg/m²) | 32 | 35 | 30 | — | — | — | — |
| Breaking strength (kg/cm²) | 64.1 | 72.1 | 62.0 | — | — | — | — |
| Breaking elongation (%) | 60 | 70 | 60 | — | — | — | — |
| Thickness of dense layer (μm) | 3.5 | 3.0 | 3.0 | — | — | — | — |
| PVP content in membrane (%) | 3.2 | 3.5 | 4.1 | — | — | — | — |
| Phosphorus clearance (ml/min) | 167 | 174 | 172 | — | 174 | 167 | 172 |

*No items could be measured because the hollow portion of the membrane was squashed or crushed.

INDUSTRIAL APPLICABILITY

The hollow fiber membrane for blood purification of the present invention exhibits excellent phosphorus-removing performance, while maintaining antithrombogenicity, by limiting the zeta potential on the inner surface of the membrane within a certain range. As a result, the membrane is useful as a hollow fiber membrane for blood purification for ameliorating bone metabolism disorders resulting from poor removal of phosphorus in the body.

In addition, since the hollow fiber membrane for blood purification of the present invention is excellent not only in the phosphorus-removing performance, but also in capability of fractionating into low-molecular-weight proteins and albumin, the blood purification apparatus using this membrane is useful for ameliorating dialysis amyloidosis and the like and can effectively contribute to amelioration of long-term dialysis complications.

The invention claimed is:

1. A hollow fiber membrane for blood purification having an integrally continuous structure from the inner membrane surface to the outer membrane surface and comprising a hydrophobic polymer and a hydrophilic polymer, and
   the hollow fiber membrane comprising a polyvinyl pyrrolidone as the hydrophilic polymer in the range of 3.0 to 5.0 wt % based on the hollow fiber membrane, exhibiting a zeta potential on the inner surface thereof of greater than −3.0 mV but less than 0 mV at pH 7.5, when measured using a sample with an embedded resin on the outer side for allowing the electrolyte solution to flow through only the inside of the hollow fiber, and using a 0.001 mol/l potassium chloride aqueous solution as an electrolyte solution.

2. The follow fiber membrane for blood purification according to claim 1, further exhibiting:
   (a) a polyvinyl pyrrolidone sieving coefficient of 45% or more in a filtration test using a polyvinyl pyrrolidone aqueous solution with a weight average molecular weight of 40,000,
   (b) a protein adsorption amount of 65 mg/m² or less,
   (c) a breaking strength of 60 kg/cm² or more, and
   (d) a breaking elongation of 60% or more.

3. The hollow fiber membrane for blood purification according to claim 2, wherein an overall mass transfer coefficient of phosphorous is 0.040 cm/min or greater.

4. The hollow fiber membrane for blood purification according to claim 2, further comprising: a thickness of a dense layer between 1 and 5 μm.

5. A blood purification apparatus comprising the hollow fiber membrane according to claim 2, installed in a cylindrical container having two nozzles for flowing a dialysate, the cylindrical container having both ends fabricated with a potting material for separating the hollow inside of the membrane from the outside by a membrane wall and the cylindrical container further having a header cap for flowing blood fitted on both ends.

6. The hollow fiber membrane for blood purification according to claim 1, wherein an overall mass transfer coefficient of phosphorous is 0.040 cm/min or greater.

7. The hollow fiber membrane for blood purification according to claim 6, further comprising: a thickness of a dense layer between 1 and 5 μm.

8. A blood purification apparatus comprising the hollow fiber membrane according to claim 6, installed in a cylindrical container having two nozzles for flowing a dialysate, the cylindrical container having both ends fabricated with a potting material for separating the hollow inside of the membrane from the outside by a membrane wall and the cylindrical container further having a header cap for flowing blood fitted on both ends.

9. The hollow fiber membrane for blood purification according to claim 1, further comprising: a thickness of a dense layer between 1 and 5 μm.

10. A blood purification apparatus comprising the hollow fiber membrane according to claim 9, installed in a cylindrical container having two nozzles for flowing a dialysate, the cylindrical container having both ends fabricated with a potting material for separating the hollow inside of the membrane from the outside by a membrane wall and the cylindrical container further having a header cap for flowing blood fitted on both ends.

11. A blood purification apparatus comprising the hollow fiber membrane according to claim 1, installed in a cylindrical container having two nozzles for flowing a dialysate, the cylindrical container having both ends fabricated with a potting material for separating the hollow inside of the membrane from the outside by a membrane wall and the cylindrical container further having a header cap for flowing blood fitted on both ends.

12. The blood purification apparatus according to claim 11, wherein the hollow fiber membrane has a phosphorus clearance of at least 180 ml/min per a membrane area of 1.5 $m^2$.

13. The follow fiber membrane for blood purification according to claim 1, wherein the hydrophobic polymer is selected from the group consisting of a polysulfone-based resin, polyether sulfone-based resin, polyamide-based resin, polyimide-based resin, polyphenyl ether-based resin, and polyphenylene sulfide-based resin.

* * * * *

UNITED STATES PATENT AND TRADEMARK OFFICE
CERTIFICATE OF CORRECTION

PATENT NO. : 9,849,427 B2  
APPLICATION NO. : 10/579449  
DATED : December 26, 2017  
INVENTOR(S) : Kuroda et al.

Page 1 of 1

It is certified that error appears in the above-identified patent and that said Letters Patent is hereby corrected as shown below:

In the Claims

At Column 24, Line 40 (Claim 2, Line 1), please change "follow fiber" to –hollow fiber–

At Column 26, Line 13 (Claim 13, Line 1), please change "follow fiber" to –hollow fiber–

Signed and Sealed this  
Ninth Day of October, 2018

Andrei Iancu  
*Director of the United States Patent and Trademark Office*